US006554810B1

(12) United States Patent
Wilk et al.

(10) Patent No.: US 6,554,810 B1
(45) Date of Patent: Apr. 29, 2003

(54) COLLAPSIBLE EMESIS CONTAINER

(76) Inventors: Peter J. Wilk, 185 W. End Ave., New York, NY (US) 10023; Karen A. Cashel, 1611 Diamond Dr., Newtown, PA (US) 18940

( * ) Notice: Subject to any disclaimer, the term of this patent is extended or adjusted under 35 U.S.C. 154(b) by 241 days.

(21) Appl. No.: 09/614,323

(22) Filed: Jul. 12, 2000

(51) Int. Cl.[7] ............................ B35D 33/00; A61F 5/44
(52) U.S. Cl. ........................... 604/323; 383/33; 383/57; 383/36; 248/99
(58) Field of Search ................................ 604/317, 321, 604/322, 323, 355; 383/33, 36, 44, 46, 48, 49, 50, 57, 58; 4/285; 248/99

(56) References Cited

U.S. PATENT DOCUMENTS

| | | | | |
|---|---|---|---|---|
| 618,624 A | | 1/1899 | Stanek et al. | |
| 3,646,935 A | | 3/1972 | Holbrook et al. | |
| 3,797,794 A | | 3/1974 | Fleury et al. | |
| 3,832,738 A | | 9/1974 | Kliemann | |
| 3,893,649 A | * | 7/1975 | Cornell et al. | 248/99 |
| 3,920,179 A | | 11/1975 | Hall | |
| RE29,321 E | | 7/1977 | Holbrook | |
| 4,182,478 A | * | 1/1980 | Etes | 229/62 |
| 4,238,448 A | | 12/1980 | Salvadori et al. | |
| 4,394,997 A | | 7/1983 | Philip | |
| 4,411,300 A | * | 10/1983 | Rico | 150/51 |
| 4,550,440 A | * | 10/1985 | Rico | 383/33 |
| 4,930,997 A | | 6/1990 | Bennett | |
| 4,950,247 A | | 8/1990 | Rosenblatt | |
| 4,990,145 A | | 2/1991 | Fleury | |
| 4,995,386 A | | 2/1991 | Ng | |
| 5,045,076 A | | 9/1991 | Pierce | |
| 5,049,273 A | | 9/1991 | Knox | |
| 5,050,616 A | | 9/1991 | Wolff et al. | |
| 5,062,835 A | | 11/1991 | Maitz et al. | |
| 5,067,821 A | | 11/1991 | Young | |
| 5,098,418 A | | 3/1992 | Maitz et al. | |
| 5,112,322 A | | 5/1992 | Hathaway | |
| 5,171,224 A | | 12/1992 | Tucker | |
| 5,188,622 A | | 2/1993 | Müller et al. | |
| 5,331,689 A | | 7/1994 | Haq | |
| 5,354,132 A | * | 10/1994 | Young et al. | 383/49 |
| 5,356,398 A | * | 10/1994 | Willis | 604/321 |
| 5,599,332 A | | 2/1997 | Cashel | |
| 5,971,969 A | | 10/1999 | Cashel | |
| 6,116,780 A | * | 9/2000 | Young et al. | 383/44 |
| 6,164,821 A | * | 12/2000 | Randall | 383/34 |
| 6,345,911 B1 | * | 2/2002 | Young et al. | 383/6 |

FOREIGN PATENT DOCUMENTS

| | | | | |
|---|---|---|---|---|
| JP | 08275908 A | * | 10/1996 | A47K/11/04 |
| SE | WO 98/26868 | * | 6/1999 | B65F/1/00 |

OTHER PUBLICATIONS

Sporty's Pilot shop, "Little John & Convenience Bag", p. 70, Nov. 1995—Feb. 1996.

* cited by examiner

*Primary Examiner*—Dennis Ruhl
*Assistant Examiner*—Michael G. Bogart
(74) *Attorney, Agent, or Firm*—R. Neil Sudol; Henry Coleman; William Sapone

(57) ABSTRACT

A container for the collection and disposal of emesis comprises a rigid frame and a flexible bag. The frame and the bag are typically stored as separate parts prior to use and assembled just prior to or in anticipation of a use. Subsequent to use the bag is dissembled from the frame and sealed and disposed of, with the frame optionally reused or disposed of. Optionally the frame and bag are disposed of as a unit without subsequent disassembly. Frames, bags, and other ancillary parts of the unit are inexpensively manufactured of molded polymers or plastics, and are inexpensive enough for single use as warranted.

16 Claims, 4 Drawing Sheets

COLLAPSIBLE EMESIS CONTAINER

BACKGROUND OF THE INVENTION

This invention relates to an emesis container.

Emesis, or contents of the stomach when eliminated by reflux through the esophagus, is a noxious substance whose collection and disposal in institutional settings is an unpleasant reality. In addition to causing more or less unpleasant sensations in those charged with its handling, emesis is or is perceived to be an agent of transmission of potentially harmful biological agents. It may contain bacteria or toxins implicated in food poisoning, and in some patients may also contain blood, with an associated risk of blood-borne pathogens. Therefore there is a demand for products which permit a neat containment of emesis and minimize a possibility of exposure for hospital or other institutional staff.

Impermeable paper bags, or "air-sickness" bags, provided with integral metal twist closures are known. While compact and inexpensive, these bags depend on a manual dexterity of a patient to hold them in place over a mouth region during an episode of sickness. It is considerably more difficult for a second person to hold them in position, along with aiding in a proper positioning of a patient's head in a case of a manually incompetent or semi-conscious patient. If the bag not firmly held to a patient's face, there is a possibility of splashing during use. Spillage after use is also a problem.

Larger, more robust, rigid plastic containers are known which overcome some of these difficulties. The containers may be provided with a screw on cap to be installed after use, and internal baffles or splash guards, which also function to limit spillage in an event an uncapped used container is inadvertently laid on a side or upended. These rigid containers, while superior to simple air-sickness bags in function, require a significant mount of storage space because of their rigidity. There is therefore a demand for a collection device which will overcome some or most of the problems of paper bags in emesis collection, while still maintaining a desirable property of compact storage.

OBJECTS OF THE INVENTION

It is an object of the invention to provide a method and device for collecting emesis from a patient.

It is a further object of the invention to provide a method and device for collecting emesis which reduces splashing in use.

It is yet a further object of the invention to provide a method and device for collecting emesis which reduces a possibility of backflow or spillage.

Still a further object of the invention is to provide a substantially sanitary method and device for the collection and disposal of emesis.

Yet another object of the invention is to provide a method and device for the collection and disposal of emesis which requires a small volume of materials to be stored on hand prior to use.

These and other objects of the invention will become apparent from a consideration of the specification and drawings which follow.

SUMMARY OF THE INVENTION

A container for the collection and disposal of emesis comprises, in accordance with the present invention, a rigid frame and a flexible bag. The frame and the bag are, in most embodiments, stored as separate parts prior to use, and combined into a unified assembly just prior to or in anticipation of a use, as for example, in being assembled and staged on a bedside table in an institutional setting. Subsequent to use, in some embodiments, the bag is dissembled from the frame and sealed and disposed of, with the frame optionally reused or disposed of. In other embodiments, the frame and bag are disposed of as a unit, without subsequent disassembly. Frames, bags, and other optional ancillary parts of the unit are inexpensively manufactured of molded polymers or plastics, in a preferred embodiment, and are inexpensive enough for single or limited multiple uses, as warranted.

When the frame, which may be multiple part or single part, and a bag are assembled, or, in one embodiment, when delivered in a single pre-assembled unit, the frame serves to hold a mouth or rim of the bag open. The frame includes a loop or closed geometric figure, as a square, polygon or circle, which defines a shape of the open bag mouth. The frame is also optionally provided with a splash guard or baffles exemplarily in a form of flaps or a funnel, which extends from an inner circumference of the loop or closed figure into an interior of the bag. The splash guard serves to limit splashing on use and spillage on inadvertent positioning of a used unit in an orientation which would otherwise spill emesis. The baffles may take the form of opposing flaps biased to be angled into an opening of the bag, which come together in a closed rest configuration, but may be opened by a passage of liquid or semi-solids. The baffles in this case function as a check valve or one-way valve.

The baffles or baffle may also be a single molded piece in form of a frustrated or truncated apical geometric solid, such as a cone or pyramid. Such shapes, when hollow, are conventionally known as funnels. While not providing a seal against backflow, a funnel may prevent exit of material under many angles, and even complete inversion of the bag, if the inversion is not too rapid.

One optional accessory part of an emesis containment unit in accordance with the present invention is a stand. The stand serves to keep an assembled unit in an orientation or position ready for use by a patient, typically maintaining an opening of the bag substantially vertical, and possibly positioned on a bedside table. The stand, which is also disposable, may be snapped onto an element of the frame. Optionally a more permanent, stand, such a modified bedside drip bag stand or beside reading table, may be employed by means of a modified bracket design to hold an assemble frame and emesis bag in position and orientation ready for use. The patient may then use the unit by turning his head and leaning to one side in bed.

Another optional accessory part of an emesis containment unit in accordance with the present invention is a handle. A handle is conveniently built into an element of the frame. A used emesis bag may thereby be conveniently carried by institutional staff without contact with parts of the unit likely to have been contaminated by emesis. The handle also conveniently allows manipulation of a partially full bag, which otherwise lacks convenient points or areas of support.

A number of methods of attachment of a disposable emesis bag to a frame holding a mouth or rim of the bag open are contemplated. In the following description, the words "mouth" and "rim" are used partially interchangeably in referring to a region surrounding an opening in the bag, but more precisely "mouth" refers abstractly to the opening or geometric shape associated with the opening, while "rim" refers more specifically to a region of material in a vicinity of the mouth, including a defining edge.

In a most simple embodiment a bag and a frame are shipped as a single pre-assembled unit. The bag may be joined to the frame by methods known in the art to fuse or seal plastic parts together including welding or gluing. The frame in this case remains rigid or semi-rigid while the bag or container is flexible, and may be folded compactly prior to use. In this way there is a substantial space saving over storage of a completely rigid container. A factory assembly of bag and frame allows achievement of a uniform and reliable seal at this joint. In this simplest embodiment the frame may also be provided with an integral baffle or splash guard. When the frame is square in shape, the baffle may be in a form of a truncated rectangular pyramid, or a more elegant shape tapering from a rectangular base to a circular opening. Provision of a baffle will increase storage space requirements for assembled units, but the units may still be stacked in a box ready for use, with bags collapsed between the units.

This pre-assembled embodiment may also be inserted into a disposable or permanent base assembly. Other embodiments of the invention are delivered to an end user in a greater number of component parts, and allow an increased flexibility of partial reuse clean or serviceable parts, and accompanying reduction in storage volume of the unassembled parts. These further embodiments principally include assemblies comprising a first or inner frame part, a second or outer frame part, and a separate flexible bag or receptacle. The unit is assembled in situ by snapping together first and second frame parts, with a rim of the bag trapped between, or "sandwiched" by the frame parts.

DETAILED DESCRIPTION

Figure 1:
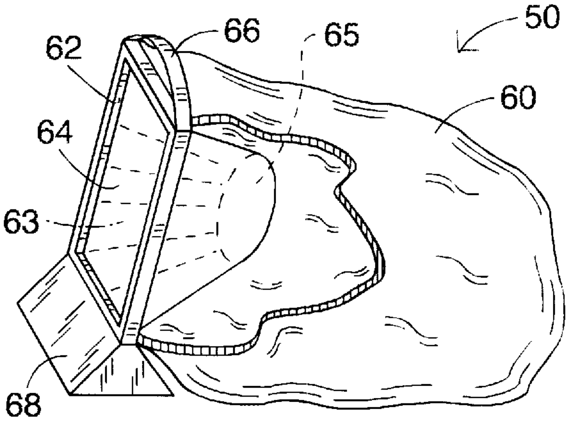
FIG. 1 is a schematic perspective of a unit emesis container in accordance with the present invention.
Figure 2:
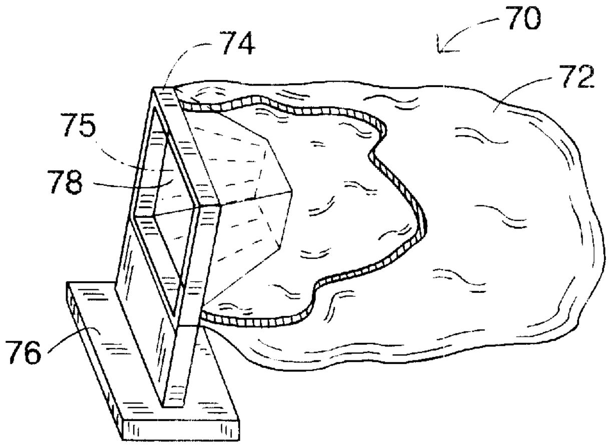
FIG. 2 is a schematic perspective of a second unit emesis container in accordance with the present invention.

As shown in FIG. 1, a single piece unit 50 comprises a frame 62 fused or glued to a flexible bag 60 at a mouth of the bag (not separately designated) to hold the mouth open. The frame defines an opening 63, and also comprises a handle 66 and a funnel or baffle 64 for directing a flow of emesis (not shown) into bag 60, limiting splashing, and preventing backflow. Unit 50 is snapped into a stand 68 to ready the unit for use, or preposition the unit on a bedside table. A similar unit is shown at 70, in a modified embodiment. A frame 74 defining an opening 75 is fused or glued to a flexible bag 72, and also comprises a baffle 78. It may be seen that baffle 78 is in a form of a truncated rectangular pyramid, while baffle 64 tapers from a square mouth (not designated) at frame 62 to a circular throat 65. Frames 62 and 74 are made from a molded polymeric composition, such as polyethylene, and are substantially rigid.

Figure 3:
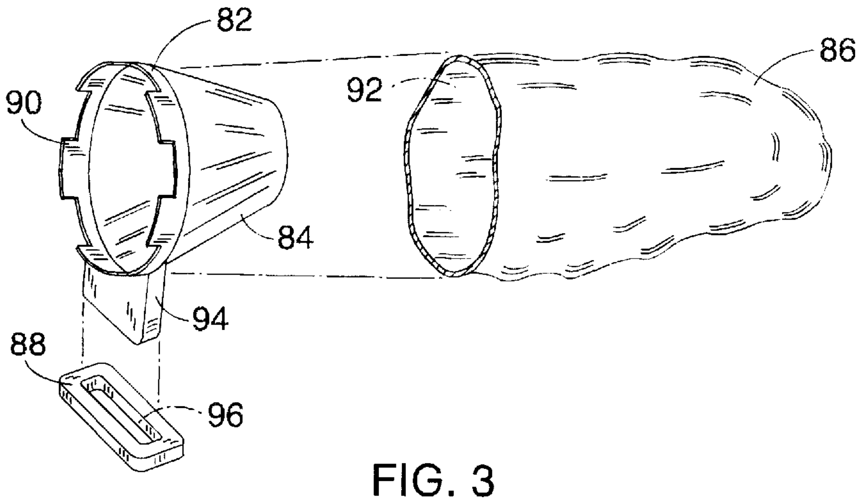
FIG. 3 is a exploded schematic perspective of a third emesis container in accordance with the present invention, prior to final assembly.
Figure 4:
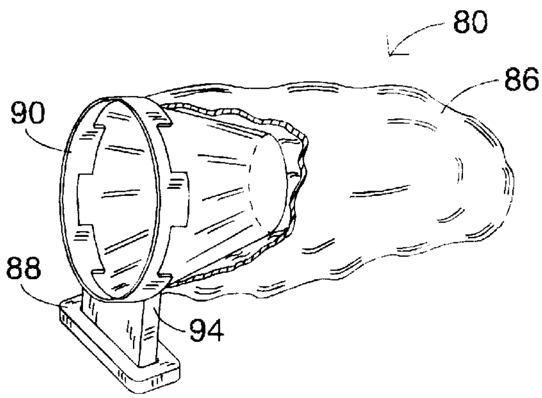
FIG. 4 is a schematic perspective of a the emesis container of FIG. 3, assembled.

An alternative assembly is shown at 80 in FIG. 4. As seen in FIG. 3, a generally circular or ring-shaped frame 82 is provided with foldable snap-lock tab elements 90 with which to engage a flexible bag 86. An integral baffle 84, generally in a form of a truncated cone, is joined to frame 82, and slips within a mouth 92 of bag 86 prior to an engagement of the snap-lock elements. A tab 94 attached to frame 82 snaps into a slot 96 in a base plate 88 to complete assembly. Completed unit 80 is shown in FIG. 4, with attached base plate.

Alternative means for attaching the bag to the frame in the embodiment of FIG. 3 may be provided. For instance, an adhesive strip may be covered with a removable backing strip, the backing removed just prior to or in a course of final assembly; the adhesive strip may be located on the frame, the bag, or on a third tape element (none shown). Alternatively, the bag and frame may be provided with complementary continuous molded zipper style closures (not shown), of a sort familiar from food storage bags, which closures are pressed together in order to form a seal of bag to frame as a step in unit assembly. Still alternatively, a plurality of micro eye and hook, or other styles of non-continuous or non-sealing cooperating locking elements, such as polymeric push-lock fasteners of a type familiar from rubberized rain gear (none shown), may be employed in conjunction with an auxiliary adhesive tape seal, for ease and security of assembly combined with a positive seal. These alternatives are mentioned to illustrate that other means of closure known in the art are contemplated along with locking tabs.

Figure 5:
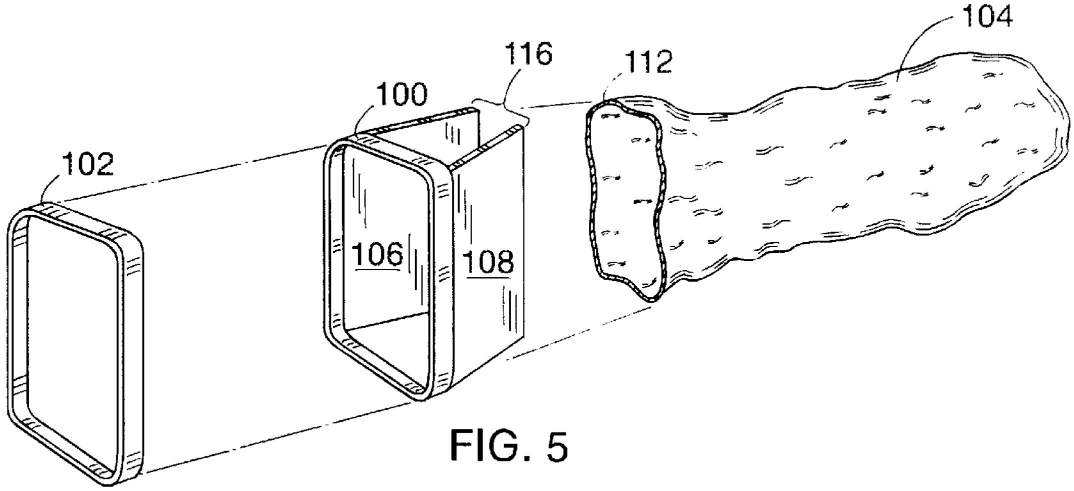
FIG. 5 is a schematic exploded perspective of a fourth emesis container in accordance with the present invention, prior to final assembly.

Two further embodiments of emesis containers, along with methods of assembly, are shown in FIG. 5 et seq. In a first additional embodiment a first frame member 100 and a second frame member 102 are pre-staged next to a flexible waterproof bag 104 having an edge or lip 112. Frame member 100 has integrally attached flaps or valves 106, 108 (FIG. 5), which serve as baffles tending to prevent a backflow of emesis; valves 106, 108 are biased to form a loosely closed relatively narrow throat 116.

Figure 6:
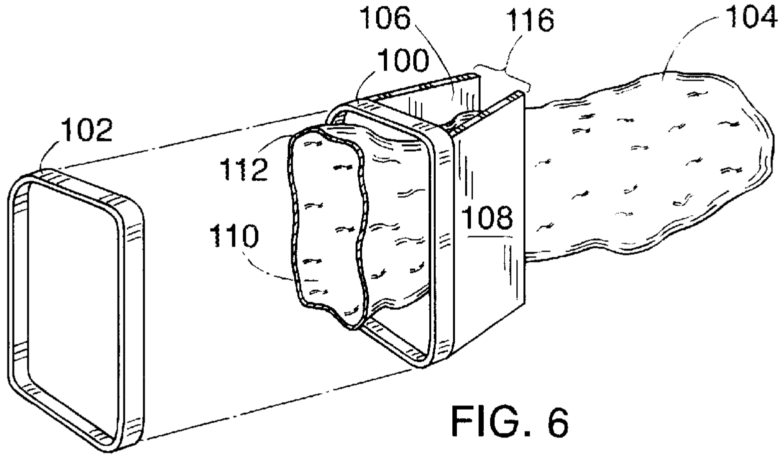
FIG. 6 is a schematic perspective of the emesis container of FIG. 5, showing a result of an initial assembly step.
Figure 7:
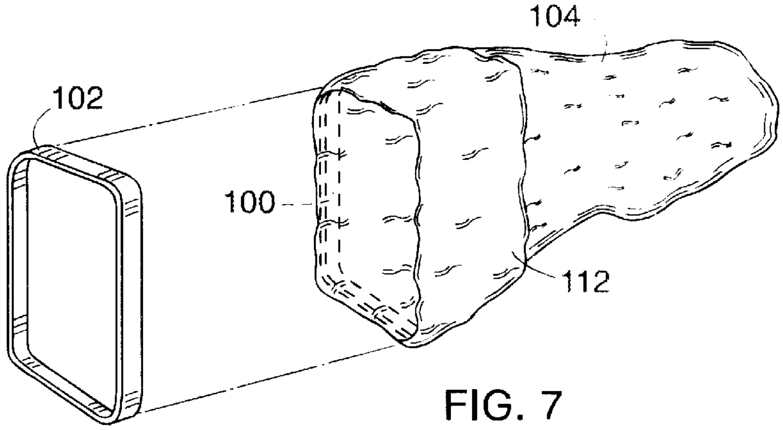
FIG. 7 is a schematic perspective of the emesis container of FIG. 5, showing a result of an subsequent assembly step.
Figure 8:
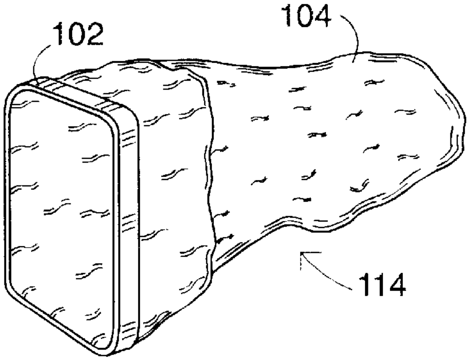
FIG. 8 is a schematic perspective the emesis container of FIG. 5, showing a result of an final assembly step, completing a functional unit.

In a first stage of in situ assembly (FIG. 6) bag 104 is passed between valves or flaps 106, 108, while a mouth 110 of the bag, defined by rim 112, is left protruding from first frame member 100. In a second stage of in situ assembly of an emesis container (FIG.7), rim 112 of bag 104 is folded back over outside surfaces (not separately designated) of flaps 106, 108, covering frame element 100. Finally, the second frame member 102 is snapped over first frame member 100, trapping or "sandwiching" bag 104 between them and forming a single assembled unit 114 (FIG. 8). Flaps or valves 106, 108 normally close a loosely constricted throat (not seen) in bag 104 corresponding to throat 116, thus tending to eliminate splashing and backflow of emesis. The construction of FIGS. 5–8 may also be optionally provided with a handle or a base (not shown) analogous to corresponding features in FIGS. 1–4.

Figure 9:
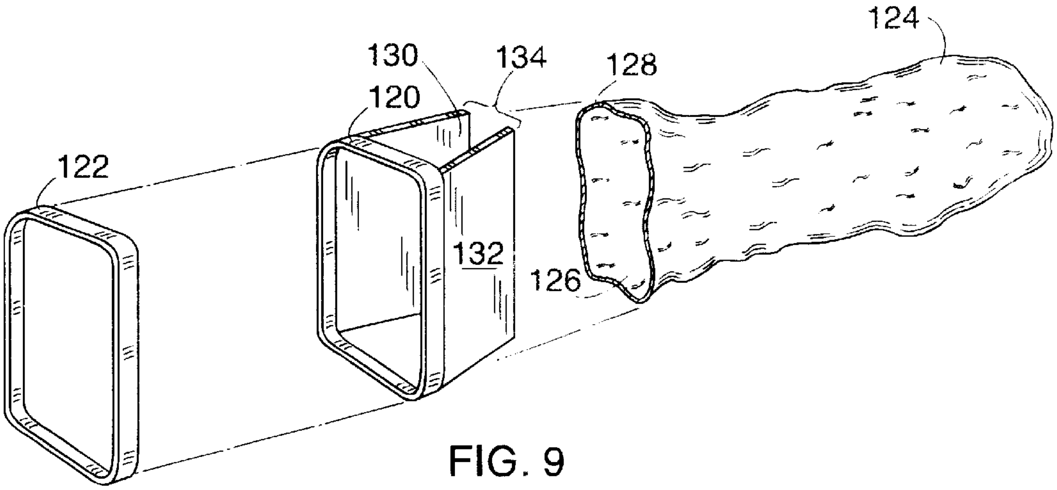
FIG. 9 is a schematic exploded perspective of a fifth emesis container in accordance with the present invention, prior to final assembly.
Figure 10:
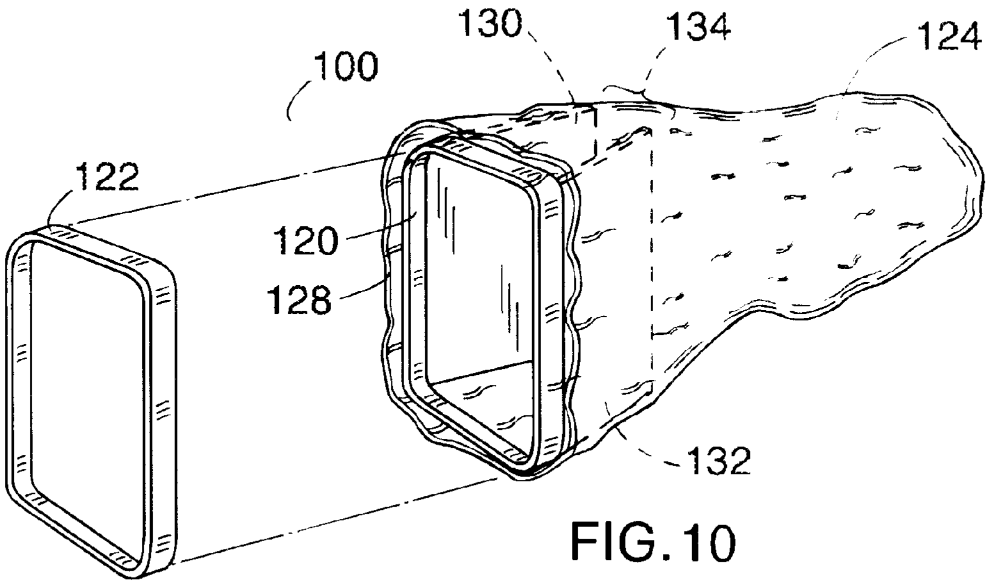
FIG. 10 is a schematic perspective of the emesis container of FIG. 9, showing a result of an initial assembly step.
Figure 11:
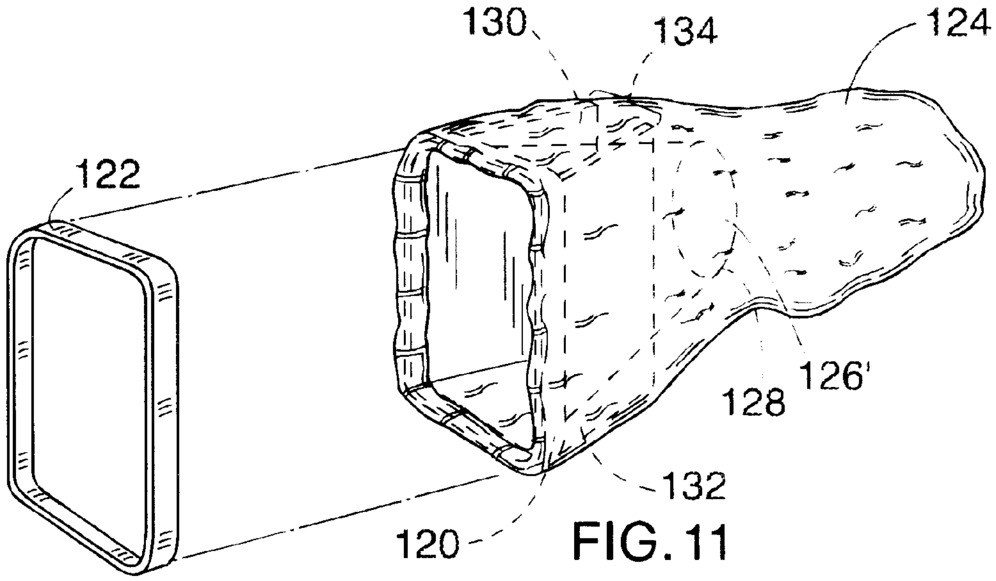
FIG. 11 is a schematic perspective of the emesis container of FIG. 9, showing a result of an subsequent assembly step.

A second additional embodiment of an emesis container and a corresponding method of assembly are illustrated in FIGS. 9–11. A first frame member 120 and a second frame member 122 are disposed in proximity to a flexible bag 124 (FIG. 9) prior to an in situ assembly of the emesis container or receptacle, similar to an arrangement of FIG. 5. First frame member 120 has attached flaps or valves 130 biased to form a relatively narrow passage or throat 134. Assembly of this embodiment deviates from an assembly of the embodiment of FIG. 5 in that frame member 120 is inserted (FIG. 10) into a mouth 126 of bag 124, defined by an rim 128. Following insertion of first frame member 120 into the mouth of bag 124, the rim is reentrantly tucked (FIG. 11) through an aperture (not separately designated) in frame element 120, past throat 134 formed by flaps 130, 132, and into a secondarily formed mouth or throat 126', interior to bag 124. Assembly is subsequently completed by snapping second frame element 122 onto element 120, thus trapping the bag and forming a single unit (step not shown), analogous to a step resulting in the assembly 114 of FIG. 8.

Other embodiments may be readily conceived of by the designer adept in product fabrication. For example, more complicated arrangements of flaps or valves may be employed, and other shapes of integral one piece baffles may be utilized in addition to those shown. Handles, bases or stands, and other methods of support or attachment may be added ad libitum to any of the embodiments disclosed herein. The circular or ring-shaped frame element or FIG. 3 and the substantially square or rectangular frame elements of FIGS. 1 and 2 may be replaced by polygonal or other closed shapes, such as ovoid or egg shaped, in defining and maintaining the opening of a flexible bag.

Therefore the embodiments described in detail are proffered by way of example of an invention whose scope is determined by the claims.

What is claimed:

1. An emesis container comprising:

a substantially rigid frame defining a substantially square opening;

a flexible bag having a mouth, the bag being attached to the frame, the frame being located at the mouth of the bag to hold the mouth open; and a baffle mounted on the frame about an inner circumference of the opening and projecting into the mouth of the bag for inhibiting an egress through said opening of fluid material collected in said bag.

2. The container of claim 1, further comprising means on at least one of the frame and the bag for attaching the bag to the frame.

3. The container of claim 2 wherein the frame is a first frame part and the means for attaching includes a second frame part attached to the first frame part, the bag being sandwiched in part between the first frame part and the second frame part.

4. The container of claim 2 wherein the means for attaching includes a plurality of cooperating locking elements.

5. The container of claim 4 wherein the locking elements are all located on the frame.

6. The container of claim 4 wherein the locking elements include foldable snap-lock tab elements.

7. The container of claim 1 wherein the bag has a mouth portion folded over the frame.

8. The container of claim 1, further comprising at least one flap pivotably mounted to the frame to cover the opening and the mouth in response to an offered egress of emesis from the bag, thereby at least inhibiting the egress of the emesis from the bag.

9. The container of claim 1 wherein said baffle takes the form of a funnel attached to the frame and extending into the bag.

10. The container of claim 1, further comprising a handle connected to the frame.

11. The container of claim 1, further comprising a base connected to the frame along one side thereof, to maintain the frame in a substantially vertical orientation.

12. A container for receiving emesis, comprising:

an inner frame part substantially bounding a substantially square opening;

an outer frame part, engageable over the outer periphery of the inner frame;

a flexible receptacle bag having a mouth defined by a rim;

wherein the inner and outer frame parts are engaged and the rim of the flexible receptacle bag is sandwiched between the inner frame and the outer frame parts; and a baffle mounted on the inner frame part about an inner circumference of the opening and projecting into the mouth of the bag for inhibiting an egress through said opening of fluid material collected in said bag.

13. The container of claim 12 wherein the baffle comprises a pair of flaps foldably mounted to opposing sides of an inner periphery of said opening in the inner frame, having a rest configuration of a pair of partially open doors.

14. The container of claim 12 wherein the baffle comprises a funnel.

15. The container of claim 12 wherein a substantial portion of the bag is inserted through the opening in the inner frame part and a rim of the bag is folded back over the inner frame part beneath the outer frame part.

16. The container of claim 12 wherein the inner frame part is inserted into the mouth of the bag, and the rim of the bag is reentrantly folded back over the inner frame part into a secondarily formed throat.

* * * * *